US006398722B1

United States Patent
Mitsumori et al.

(10) Patent No.: US 6,398,722 B1
(45) Date of Patent: Jun. 4, 2002

(54) ENDOSCOPE RUBBER PART HAVING A PERFLUOROMONOMER STRUCTURE

(75) Inventors: Naotake Mitsumori; Joji Watanabe, both of Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 0 days.

(21) Appl. No.: 09/502,217

(22) Filed: Feb. 11, 2000

(30) Foreign Application Priority Data

Feb. 19, 1999 (JP) .................................. 11-041677

(51) Int. Cl.[7] .................................................. A61B 1/00
(52) U.S. Cl. ..................................................... 600/133
(58) Field of Search ........................................ 600/133

(56) References Cited

U.S. PATENT DOCUMENTS

| | | | | |
|---|---|---|---|---|
| 5,428,096 A | * | 6/1995 | Fukunaga | 524/440 |
| 5,697,888 A | * | 12/1997 | Kobayashi et al. | 600/159 |
| 5,707,763 A | * | 1/1998 | Shimizu et al. | 429/217 |
| 5,871,441 A | * | 2/1999 | Ishiguro et al. | 600/159 |
| 6,060,167 A | * | 5/2000 | Morgan et al. | 428/422 |
| 6,132,468 A | * | 10/2000 | Mansmann | 623/20.16 |
| 6,221,970 B1 | * | 4/2001 | Morken et al. | 525/326.3 |
| 6,262,209 B1 | * | 7/2001 | Kapeliouchko et al. | 526/247 |

OTHER PUBLICATIONS

Whelan, T., "Polymer Technology Dictionary", 1994, Chapman & Hall, p. 162.*

* cited by examiner

*Primary Examiner*—John P. Leubecker
(74) *Attorney, Agent, or Firm*—Oliff & Berridge, PLC

(57) ABSTRACT

In an endoscope apparatus, a suction button is detachable from a manual control part, and rubber parts such as O-rings and a knob are attached to the suction button. The rubber parts are made of a perfluoromonomer rubber material that is obtained by vulcanizing a material having a perfluoromonomer structure in which an average molecular weight is not greater than 2000. Thus, the rubber parts have excellent chemical resistance, heat resistance and mechanical strength. Therefore, the suction button can be both disinfected with new types of disinfectant having powerful oxidizing properties and sterilized in an autoclave.

4 Claims, 3 Drawing Sheets

F I G. 3
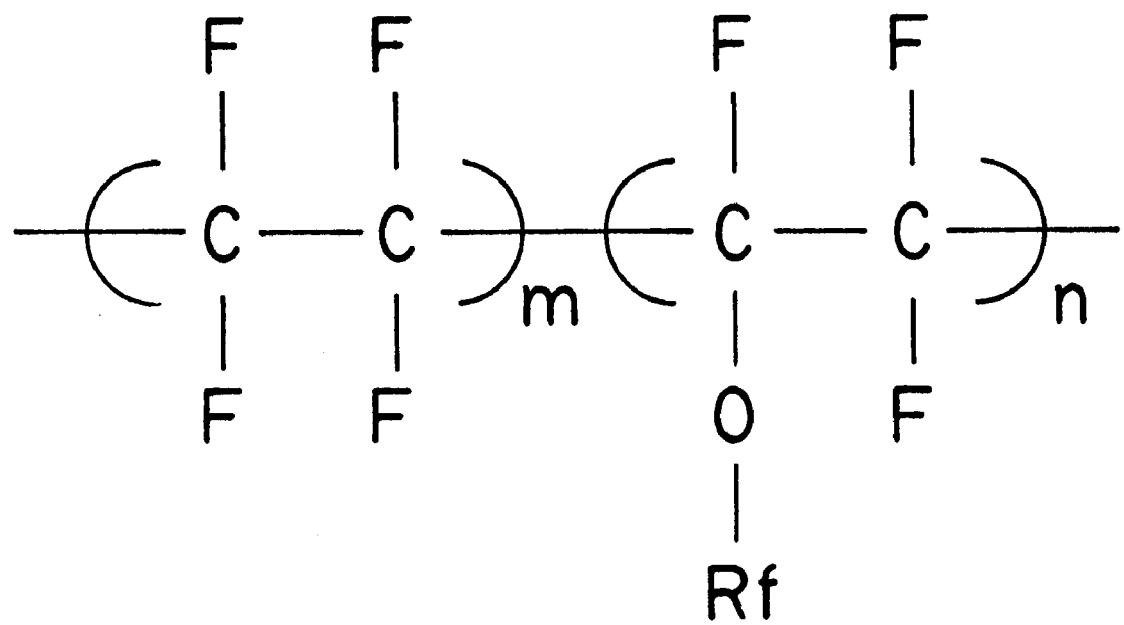

ENDOSCOPE RUBBER PART HAVING A PERFLUOROMONOMER STRUCTURE

BACKGROUND OF THE INVENTION

1. Field of the Invention

This invention relates generally to an endoscope apparatus, and more particularly to an endoscope apparatus that can be disinfected with satisfactory results.

2. Description of Related Art

An endoscope apparatus is provided with members such as an air/water supply button and a suction button, which are arranged at a scope operation part, a forceps aperture plug used for a forceps aperture formed in a scope holding part, a variety of caps provided at an auxiliary water supply channel, etc., a water supply tank, and the like provided as the need arises. These members include many parts made of conventional rubber material such as nitrile rubber (NBR), silicone rubber and fluorocarbon rubber (copolymer of vinylidenefluoride and hexafluoropropylene).

The endoscope apparatus for medical use must be disinfected completely. The endoscope apparatus is ordinarily disinfected according to guidelines issued by medical societies and the like. According to the guidelines, the endoscope must be disinfected with the highest standards, and glutaraldehyde and ethylene oxide gas (EOG) are recommended as disinfectant. However, these disinfectants are highly toxic, and they may damage the health of the operator and may cause damage to the environment as well. It is therefore undesirable to use these disinfectants.

Accordingly, new types of disinfectant have been increasingly used such as peracetic acid ($CH_3COOOH$), plasma of hydrogen peroxide ($H_2O_2$), and acid water, which after use become water, air or harmless substances. These new types of disinfectant have powerful oxidizing properties, and may cause the rubber parts of the endoscope to corrode. For example, NBR cannot resist the new types of disinfectant at all. Although fluorocarbon rubber has relatively high chemical resistance, it may crack, swell and the like if the endoscope apparatus is exposed to the new types of disinfectant for a long time. Silicone rubber has a high chemical resistance; however, it has a low mechanical strength and is not suitable for all rubber parts of the endoscope apparatus.

Ethylene-propylenediene terpolymer (EPDM) has both a high chemical resistance and a high mechanical strength, and it has been increasingly used for the rubber parts of the endoscope apparatus. EPDM, however, is easily affected by heat and is only resistant to 135° C. under normal pressure. Hence, the rubber parts made of EPDM are not suitable for the autoclave sterilization in which steam of 132° C. under pressure of 200 kPa effects sterilization. The autoclave sterilization is authorized by the guidelines. Recently, at least the parts detachable from the body of the endoscope apparatus are required to be sterilized in the autoclave.

SUMMARY OF THE INVENTION

It is therefore an object of the present invention to provide an endoscope apparatus that can be sterilized in the autoclave and disinfected with the new types of disinfectant having powerful oxidizing properties such as peracetic acid.

To achieve the above object, the present invention provides an endoscope comprising: a rubber part made of vulcanized rubber material having a perfluoromonomer structure of which an average molecular weight is not greater than 2000.

The material having the perfluoromonomer structure is a copolymer that is obtained by completely replacing hydrogen atoms with fluorine atoms. The perfluoromonomer material is usually used as fluoroplastics, and the usual perfluoromonomer material has no rubber properties such as ductility and elasticity.

According to the present invention, the rubber parts of the endoscope are made of a perfluoromonomer rubber material, which is softened by using the perfluoromonomer material with average molecular weight of not greater than 2000 and is vulcanized. The perfluoromonomer rubber material has rubber characteristics such as ductility and elasticity and the same characteristics as fluoroplastics. More specifically, the perfluoromonomer rubber material has a high heat resistance, a high chemical resistance, a high mechanical strength and a high smoothness, and is nontoxic. The endoscope of the present invention has the rubber parts made of the perfluoromonomer rubber material, and can be both sterilized in the autoclave and disinfected with the new types of disinfectant having powerful oxidizing properties.

Preferably, the average molecular weight of the perfluoromonomer rubber material is not less than 1000 in order to prevent the manufactured rubber parts from becoming softened excessively.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 3 is a view showing the structure of molecule in a perfluoromonomer rubber material.

DETAILED DESCRIPTION OF THE PREFERRED EMBODIMENT

This invention will be described in further detail by way of example with reference to the accompanying drawings.

Figure 1:
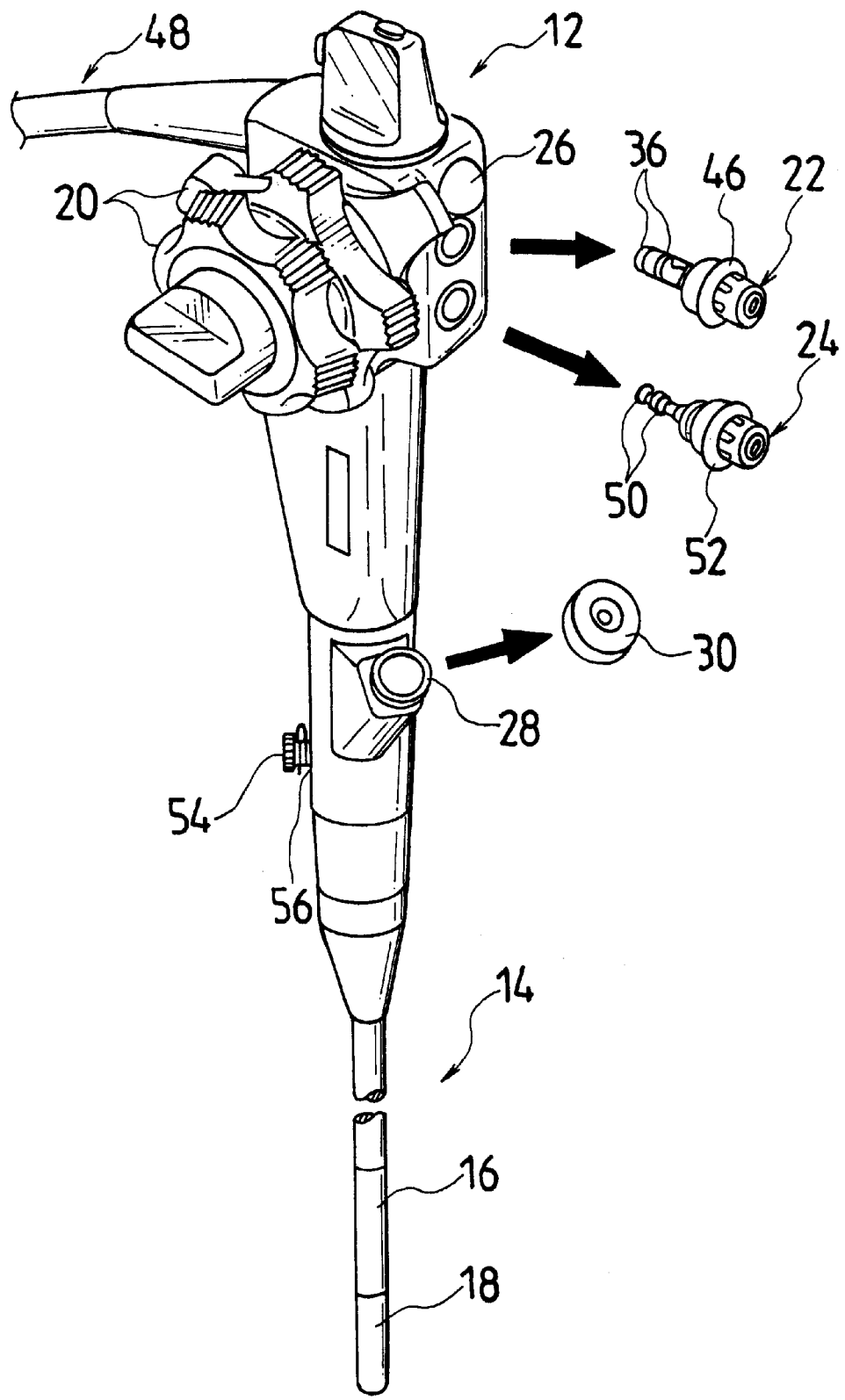
FIG. 1 is a perspective view showing a manual control part of an endoscope apparatus according to a preferred embodiment of the present invention.

FIG. 1 is a perspective view showing a manual control part 12 of an endoscope apparatus according to a preferred embodiment of the present invention.

An insertion part 14, which is inserted into a body cavity of a subject, connects to the manual control part (equivalent to the body of the endoscope apparatus) 12 in FIG. 1. A hard end part 18 is formed at the end of the insertion part 14 through a curved part 16. The curved part 16 is curved remotely by rotating a pair of knobs 20 provided at the manual control part 12.

An objective lens, a lighting aperture, an air/water supply aperture and a forceps channel (not illustrated) are provided at an end face of the hard end part 18. A solid state imaging device (e.g., CCD) is provided inside the objective lens.

A suction button 22 and an air/water supply button 24 are arranged on the manual control part 12. Pressing the suction button 22 sucks liquid such as a cleaning water, a liquid medicine and blood from the body cavity through the forceps channel. Pressing the air/water supply button 24 supplies compressed air or the cleaning water into the body cavity through the air/water supply aperture. A shutter release button 26 is provided at the manual control part 12, and an object image is recorded by pressing the shutter release button 26. Reference numeral 28 denotes a forceps aperture connected to the forceps channel, and treatment equipment such as forceps is inserted from the forceps aperture 28. Reference numeral 30 denotes a forceps aperture plug mounted in the forceps aperture 28. The forceps aperture plug 30 serves as a checkvalve to prevent backflow of gas or liquid from the body cavity, and the forceps is inserted into the body cavity through the forceps aperture plug 30. Reference numeral 54 denotes a cap, which is attached to the manual control part in the case where an auxiliary water supply aperture (or a jetting aperture or an aperture for standing the forceps) 56 is not used. Reference numeral 48 is a soft light guide part, in which a light guide or the like is provided for transmitting illumination light from a light source apparatus (not illustrated) to the objective lens of the hard end part 18.

Figure 2:
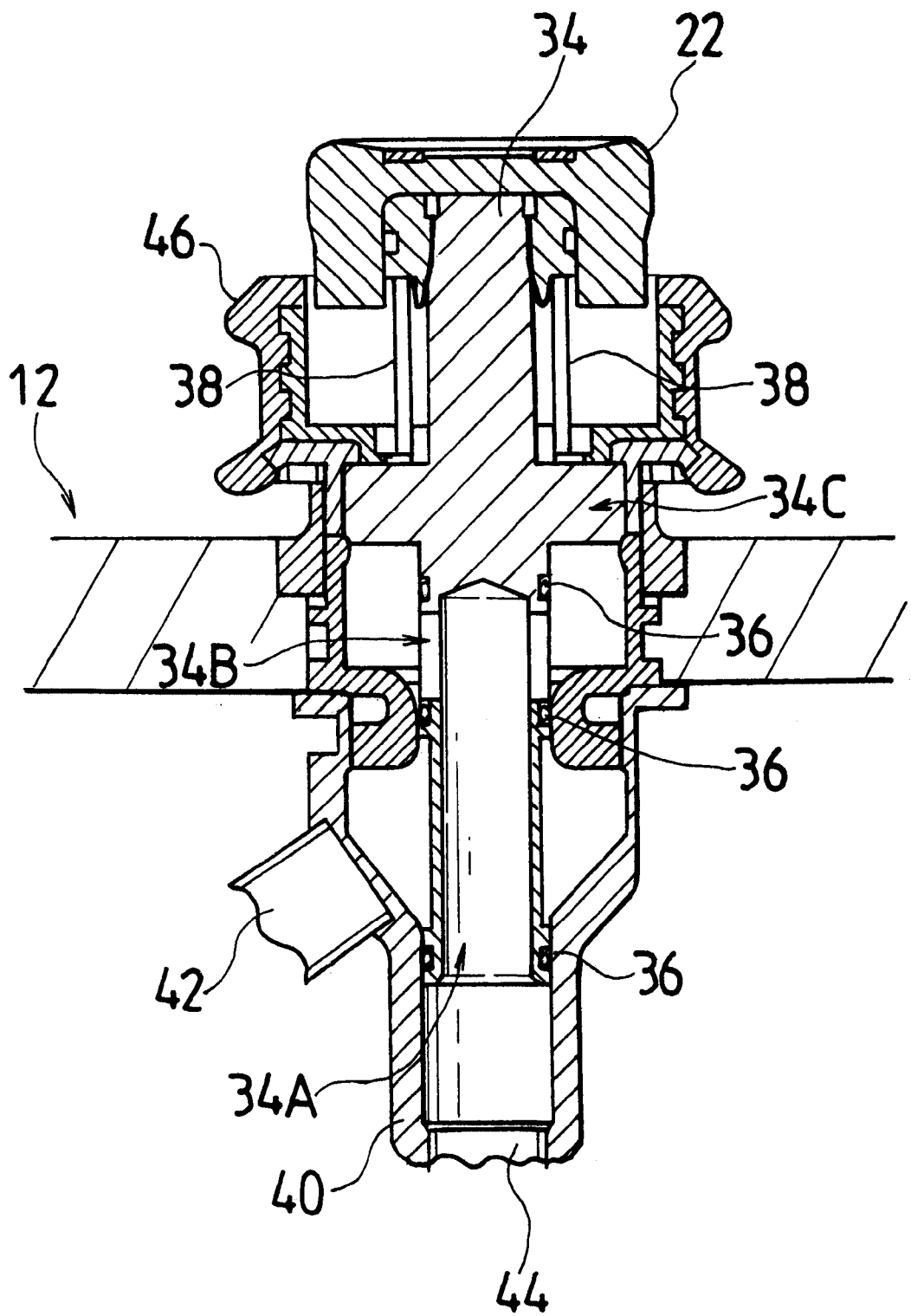
FIG. 2 is a cross-sectional view showing a suction button of the manual control part in FIG. 1.

FIG. 2 is a sectional view showing the structure of the suction button 22 in FIG. 1. In FIG. 2, the suction button 22 is not pressed.

As shown in FIG. 2, the suction button 22 is attached to the end of a cylindrical piston 34, and is pressed upward by a pressing member or spring 38. The piston 34 is detachably inserted into a cylinder 40, which is attached to the manual control part 12, through a plurality of O-rings 36 in such a manner that the piston 34 can freely slide vertically in the attached state. In the piston 34, a hole 34A is formed in the axial direction of the piston 34, and apertures 34B are formed to, connect to the hole 34A along the diameter direction of the piston 34. A collar 34C is formed on the piston 34, and an air leakage aperture (not illustrated) is formed in the collar 34C along the axial direction of the piston 34. Therefore, the inside of the cylinder 40 is connected to the outside through the hole 34A, the apertures 34B and the air leakage aperture in the state where the suction button 22 is not pressed.

The cylinder 40 of the manual control part 12 connects to a suction tube 42, which connects to the forceps channel formed at the hard end part 18 in FIG. 1. The cylinder 40 in FIG. 2 connects to a suction tube 44, which connects to a suction device (not illustrated). When the suction button 22 is pressed against a force of the pressing member 38, the suction tube 42 connects to the suction tube 44 through the hole 34A and the apertures 34B of the piston 34. Consequently, water, mucus and the like in the body cavity are sucked through a suction port provided on the hard end part 18. Reference numeral 46 denotes a knob, which is held in order to attach and detach the suction button 22 to and from the manual control part 12.

The suction button 22 and the piston 34 are made of corrosion-resistant material; e.g., plastics, aluminum coated with diamond like carbon and the like, and stainless steel. The O-rings 36 and the knob 46 are made of vulcanized perfluoromonomer rubber material having a perfluoromonomer structure described below of which average molecular weight is not greater than 2000.

FIG. 3 is a view showing the basic structure of molecule in the perfluoromonomer rubber material used for the rubber parts of the endoscope apparatus according to the present invention. The structure of molecule is called the perfluoromonomer structure. In FIG. 3, Rf represents a perfluoroalkyl group. As shown in FIG. 3, the perfluoromonomer rubber material consists essentially of carbon, fluorine and oxygen, and has the same construction as fluorocarbon resin called PFA (tetrafluoroethylene-perfluoroalkylvinylether copolymer). The perfluoromonomer material has the same property as the PFA, and has advantages as described below.

1) The perfuluoromonomer material never deteriorates even in the new types of Disinfectant, which have powerful oxidizing properties, since it is completely fluoridized and has an excellent chemical resistance.

2) The perfluoromonomer material can be applied to the autoclave sterilization, since it is capable of resisting a heat of about 300° C. (ordinarily 287° C. or less).

3) The perfluoromonomer material can be used in medical equipment such as the endoscope apparatus, since it is nontoxic.

4) The perfluoromonomer material can be used for slidable parts such as the suction button 22, since it has a small friction coefficient and has an excellent smoothness.

5) The perfluoromonomer material has a greater mechanical strength than silicone rubber.

For the reasons stated above, the perfluoromonomer material having the perfluoromonomer structure is suitable for the medical equipment. The perfluoromonomer material, however, is ordinarily used in the form of fluoroplastics, and loses the ductility and elasticity peculiar to the rubber. In the worst case, the ordinary perfluoromonomer material is plastically deformed. Hence, the ordinary perfluoromonomer material cannot be used as a substitute for conventional rubber material (e.g., EPDM).

To solve this problem, the perfluoromonomer material in this embodiment is constructed in such a manner as to have the average molecular weight of not greater than 2000, and the material is vulcanized. The less the molecular weight is, the softer the perfluoromonomer material is. Then, if the molecular weight of the perfluoromonomer material is less than that of the resin, of which the molecular weight is normally between 2100 and 9200, the rigidity of the resin is eliminated to thereby acquire the softened perfluoromonomer material Further, the perfluoromonomer material is crosslinked by the vulcanization, and a two-dimensional linear polymer becomes a three-dimensional network structure so that the perfluoromonomer material can be elastic. Thus, the perfluoromonomer rubber material is acquired. The perfluoromonomer rubber material is superior in chemical-resistance, heat-resistance and mechanical-strength, and the perfluoromonomer rubber material can be applied to both the new types of disinfectant and the autoclave sterilization. Moreover, the perfluoromonomer rubber material has a very high smoothness and can be used for slidable parts. The molecular weight and the extent of vulcanization are adjusted so that the hardness (defined in Japanese Industrial Standard K6301) of a molded perfluoromonomer rubber can be between 60 and 70. The perfluoromonomer material may be vulcanized by heating with blending crosslinking agents; e.g., peroxide such as 1,1-di (t-butylperoxy)-3,3,5-trimethylsiloxane and sulfur. The perfluoromonomer material can also be vulcanized by another reagent (e.g., amine and phenol resin) or energy (e.g., ultraviolet rays, electron beam and radial rays) other than heat.

As stated above, the O-rings 36 provided at the suction button 22 and the knob 46 are made of the above-stated perfluoromonomer rubber material, and therefore the suction button 22 removed from the manual control part 12 can be sterilized not only in the new types of disinfectant but in the autoclave.

Other parts may also be made of the perfluoromonomer rubber material. For example, the perfluoromonomer rubber material may also be used for O-rings 50 and a knob 52 of the air/water supply button 24 in FIG. 1, the forceps aperture plug 30, the cap 54 for the auxiliary water supply aperture 56 and the like, and a cap for a ground terminal to be used when high-frequency treatment equipment provided in a light guide connector or the like is used, treatment equipment such as the forceps inserted from the forceps aperture 28, a guide tube and a sliding tube for use to guide a scope insertion part of a small intestine endoscope or a large intestine endoscope into the body cavity, and a water supply tank for containing the cleaning water sent by operating the water supply button. Moreover, all rubber parts of the endoscope components may be made of the perfluoromonomer rubber material so that the entire endoscope can be both disinfected with the new types of disinfectant and sterilized in the autoclave. According to the present invention, the perfluoromonomer rubber material is preferably used for rubber parts such as a part detachable from the control part 12, which may be both disinfected with the new types of disinfectant having powerful oxidizing properties and sterilized in the autoclave.

In the present embodiment, the average molecular weight of the perfluoromonomer rubber material is not greater than 2000, and more preferably, the average molecular weight is between about 1000 and about 2000 in order to prevent the manufactured rubber parts from becoming softened excessively.

As set forth hereinabove, the rubber parts of the endoscope apparatus according to the present invention are made of the vulcanized rubber material having the perfluoromonomer structure, in which the average molecular weight is not greater than 2000. Therefore, the rubber parts can not only be sterilized in the autoclave but also be disinfected with the new types of disinfectant that have powerful oxidizing properties. This improves the disinfecting and sterilizing performance of the endoscope apparatus.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope, comprising: a rubber part made of vulcanized rubber material having a perfluoromonomer structure of which an average molecular weight is not less than 1000 and not greater than 2000.

2. The endoscope as defined in claim 1, wherein the rubber part is one of an air/water supply button and a suction button detachable from a body of the endoscope.

3. The endoscope as defined in claim 1, where the average molecular weight and a level of vulcanization of the vulcanized rubber material is adjusted such that the vulcanized rubber material has a hardness between 60 and 70.

4. The endoscope as defined in claim 1, wherein said vulcanized rubber material has a hardness between 60 and 70.

* * * * *

UNITED STATES PATENT AND TRADEMARK OFFICE
CERTIFICATE OF CORRECTION

PATENT NO.    : 6,398,722 B1
DATED         : June 4, 2002
INVENTOR(S)   : Noatake Mitsumori and Joji Watanabe It is certified that error appears in the above-identified patent and that said Letters Patent is hereby corrected as shown below:

Title page, item [54], and Column 1, lines 1 and 2,
Change the title to -- ENDOSCOPE APPARATUS --.

Signed and Sealed this

Tenth Day of December, 2002

JAMES E. ROGAN
*Director of the United States Patent and Trademark Office*